(12) United States Patent
Glezer et al.

(10) Patent No.: US 8,834,911 B2
(45) Date of Patent: Sep. 16, 2014

(54) FLOW MANIPULATION IN BIOLOGICAL FLOWS USING VORTEX GENERATORS

(75) Inventors: Ari Glezer, Atlanta, GA (US); Ajit P. Yoganathan, Tucker, GA (US); Lakshmi Prasad Dasi, Atlanta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 1442 days.

(21) Appl. No.: 11/940,497

(22) Filed: Nov. 15, 2007

(65) Prior Publication Data

US 2008/0121046 A1 May 29, 2008

Related U.S. Application Data

(60) Provisional application No. 60/865,919, filed on Nov. 15, 2006.

(51) Int. Cl.
*A61F 13/00* (2006.01)
*A61F 2/00* (2006.01)
*A61M 1/36* (2006.01)
*A61F 2/24* (2006.01)
*A61F 2/06* (2013.01)
*A61F 2/82* (2013.01)

(52) U.S. Cl.
CPC .............. *A61M 1/3675* (2013.01); *A61F 2/24* (2013.01); *A61F 2002/068* (2013.01); *A61F 2/82* (2013.01); *A61F 2/0077* (2013.01)
USPC ....................................... 424/422

(58) Field of Classification Search
None
See application file for complete search history.

(56) References Cited

U.S. PATENT DOCUMENTS

| 4,075,091 A | 2/1978 | Bellhouse ........................ 210/19 |
| 4,872,875 A | 10/1989 | Hwang ............................ 623/2 |
| 2002/0179166 A1 | 12/2002 | Houston et al. .................. 138/39 |

FOREIGN PATENT DOCUMENTS

| EP | 0 352 902 A2 | 1/1990 |
| WO | WO 2006045555 A1 * | 5/2006 |

OTHER PUBLICATIONS

International Search Report dated May 2, 2008 cited in International Application No. PCT/US2007/084816.
H.A. Simon et al., "Comparison of the Hinge Flow Fields of Two Bileaflet Mechanical Heart Valve under Aortic and Mitral Conditions", Annals of Biomedical Engineering, vol. 32, No. 12, Dec. 2004, pp. 1607-1617.
H.-L. Leo et al., "Microflow fields in the hinge region of the CarboMedics bileaflet mechanical heart valve design", The Journal of Thoracic and Cardiovascular Surgery, vol. 124, No. 3, pp. 561-574, 2002.
P.C. Lu et al., "A reevaluation and discussion on the threshold limit for hemolysis in a turbulent shear flow", Journal of Biomechanics, 34, pp. 1361-1364, 2001.

(Continued)

*Primary Examiner* — Carlos Azpuru
*Assistant Examiner* — Casey Hagopian
(74) *Attorney, Agent, or Firm* — Merchant & Gould (57) ABSTRACT

A device for use in combination with a fluid flow having a biologic component and subject to an adverse response to shear stress includes a surface in contact with the flow of the fluid. The surface has a longitudinal direction extending from a leading end toward a trailing end and aligned with a direction of the flow. The surface is susceptible to inducing boundary layer formation within the flow sufficient for a resulting shear stress to induce the response. The surface includes a surface feature sufficient to induce boundary layer tripping in the flow to retard growth of boundary layer formation along the length.

18 Claims, 9 Drawing Sheets

(56) References Cited

OTHER PUBLICATIONS

S.P. Sutera et al., "Hemolysis and Subhemolytic Alterations of Human RBC Induced by Turbulent Shear Flow", ASAIO Transactions, vol. XVIII, 335-341, 1972.

S.P. Sutera et al., "Deformation and Fragmentation of Human Red Blood Cells in Turbulent Shear Flow", Biophysical Journal, vol. 15, pp. 1-10, 1975.

L.J. Wurzinger et al., "Shear induced platelet activation, A Critical Reappraisal", Biorheology, 22, pp. 399-413, 1985.

A.M. Sallam et al., "Human red blood cell hemolysis in a turbulent shear flow: Contribution of Reynolds shear stresses", Biorheology, 21, pp. 783-797, 1984.

J.D. Hellums et al., "Blood Cell Damage by Mechanical Forces", Chapter 20, Cardiovascular Flow Dynamics and Measurements, pp. 799-822, 1977.

C.H. Brown et al., "Morphological, Biochemical, and Functional Changes in Human Platelets Subjected to Shear Stress", The Journal of Laboratory and Clinical Medicine, vol. 86, No. 3, Sep. 1975, pp. 462-474.

E.F. Bernstein et al., "Structural correlates of platelets functional damage by physical forces", Trans. Am. Soc. Artif. Intern. Organs, vol. XXIII, pp. 617-625, 1977.

C.G. Nevaril et al., "Erythrocyte Damage and Destruction Induced by Shearing Stress, Journal of Laboratory and Clinical Medicine", The Journal of Laboratory and Clinical Medicine, vol. 71, No. 5, May 1968, p. 784.

G.H. Anderson et al., "Platelet Lysis and Aggregation in Shear Fields", Blood Cells, 4,, 1978, pp. 499-511.

L.J. Wurzinger et al., "Platelet and coagulation parameters following millisecond exposure to laminar shear stress", Thrombosis and Haemostasis, 54 (2), pp. 381-386, 1985.

L.J. Wurzinger et al., "Mechanical blood trauma: an overview", Angeiologie, 38,Apr. 3-May 1986,, pp. 81-97.

L.J. Wurzinger et al., "Towards a concept of thrombosis in accelerated flow: rheology, fluid dynamics, and biochemistry", Biorheology, 22, pp. 437-449, 1985.

M. Grigioni et al., "The Power-law Mathematical Model for Blood Damage Prediction: Analytical Developments and Physical Inconsistencies", Artificial organs, 28, pp. 467-475, 2004.

J.T. Ellis et al., "An in vitro investigation of the retrograde flow fields of two bileaflet mechanical heart valves", Journal of Heart Valve Disease, vol. 5, No. 6, pp. 600-606, 1996.

A.P. Yoganathan et al., The Biomedical Engineering Handbook, Second Edition, 123 Cardiac Valve Prostheses, pp. 1847-1870, 1995.

A.P. Yoganathan et al., The Biomedical Engineering Handbook, Second Edition, 127 Cardiac Valve Prostheses, 23 pgs., 2000.

J.T. Ellis et al., "An In Vitro Study of the Hinge and Near-Field Forward Flow Dynamics of the St. Jude Medical® Regent™ Bileaflet Mechanical Heart Valve", Annals of Biomedical Engineering, vol. 28, pp. 524-532, 2000.

J. Ellis et al., "A comparison of the hinge and near-hinge flow fields of the St. Jude Medical Hemodynamic Plus and Regent bileaflet mechanical heart valves", Journal of Thoracic and Cardiovascular Surgery, 119, Jan. 2000 pp. 83-93.

B.R. Travis et al., "Bileaflet Aortic Valve Prosthesis Pivot Geometry Influences Platelet Secretion and Anionic Phospholipid Exposure", Annals of Biomedical Engineering, vol. 29, pp. 657-664, 2001.

A. Steegers et al., "Leakage flow at mechanical heart valve prosthesis: Improved washout or increased blood damage?", Journal of Heart Valve Disease, vol. 8, No. 3, May 1999, pp. 312-323.

M.M. Black et al., "Mechanical and Other Problems of Artificial Valves," Current Topic in Pathology, vol. 86, (ed. C. Berry), pp. 127-159, Springer-Verlag Berlin Heidelberg, 1994.

D. Bluestein et al., "Vortex Shedding in Steady Flow through a Model of an Arterial Stenosis and its Relevance to Mural Platelet Deposition", Annals of Biomedical Engineering, vol. 27, pp. 763-773, 1999.

D. Bluestein et al., "A squeeze flow phenomenon at the closing of a bileaflet mechanical heart valve prosthesis", Journal of Biomechanics, vol. 27, No. 11, pp. 1369-1378, 1994.

H. Choi et al., "Direct Numerical-Simulation of Turbulent-Flow over Riblets", Journal of Fluid Mechanics, vol. 255, pp. 503-539, 1993.

M.J. Walsh, "Riblets as a Viscous Drag Reduction Technique", AIAA Journal, vol. 21, No. 4, Apr. 1983, pp. 485-485.

F.E. Fish et al., "Passive and active flow control by swimming fishes and mammals", Annual Review of Fluid Mechanics, 38, pp. 193-224, 2006.

J.C. Lin, "Review of research on low-profile vortex generators to control boundary-layer separation", Progress in Aerospace Sciences, 38, pp. 389-420, 2002.

K. Zaman et al., "The effect of vortex generators on a jet in a crossflow", American Institute of Physics, Physics of Fluids, 9 (1), Jan. 1997, pp. 106-114.

K. Zaman et al., "Control of an Axisymmetrical Jet Using Vortex Generators", American Institute of Physics, Physics of Fluids, 6 (2), Feb. 1994, pp. 778-793.

A. Lecuona et al., "Near field vortex dynamics in axially forced, co-flowing jets: quantitative description of a low-frequency configuration", European Journal of Mechanics B-Fluids, 21, pp. 701-720, 2002.

P. Rodriguez-Aumente et al., "Near field vortex dynamics in axially forced, laminar, co-flowing jets: a descriptive study of the flow configurations", European Journal of Mechanics B-Fluids, 20, pp. 673-698, 2001.

B.R. Travis et al., "The Sensitivity of Indicators of Thrombosis Initiation to a Bileaflet Prosthesis Leakage Stimulus", Journal of heart valve disease, vol. 10, No. 2, Mar. 2001, pp. 228-238.

E.M. Baudet et al., "A 5-1/2-Year Experience with the St. Jude Medical Cardiac-Valve Prosthesis—Early and Late Results of 737 Valve Replacements in 671 Patients", The Journal of Thoracic and Cardiovascular Surgery, vol. 90, No. 1, Jul. 1985, pp. 137-144.

B.C. Chang et al.,"Long-term results with St. Jude Medical and CarboMedics prosthetic heart valves", Journal of Heart Valve Disease, vol. 10, No. 2, Mar. 2001, pp. 185-194.

M. Ibrahim et al., "The St. Jude Medical Prosthesis—a Thirteen-Year Experience", Journal of Thoracic and Cardiovascular Surgery, vol. 108, No. 2, Aug. 1994, pp. 221-230.

R. G. Masters et al., "Comparative Results with the St. Jude Medical and Medtronic-Hall Mechanical Valves", Journal of Thoracic and Cardiovascular Surgery, vol. 110, No. 3, Sep. 1995, pp. 663-671.

A. El-Banayosy et al., "Device and patient management in a bridge-to-transplant setting", Annals of Thoracic Surgery, 71, pp. S98-S102, 2001.

E.L. Kukuy et al., "Long-term Mechanical Circulatory Support", Cardiac Surgery in the Adult, Second Edition, McGraw-Hill, New York, Chapter 62, pp. 1491-1505, 2003.

K. Minami et al., "Morbidity and outcome after mechanical ventricular support using thoratec, novacor, and HeartMate for bridging to heart transplantation", Artificial Organs, 24 (6), pp. 421-426, 2000.

S. W. Day et al., "PIV measurements of flow in a centrifugal blood pump: Steady flow", Journal of Biomechanical Engineering-Transactions of the Asme, vol. 127, Apr. 2005, pp. 244-253.

K. Kawahito et al., "Platelet activation in the Gyro C1E3 centrifugal pump: Comparison with the Terumo Capiox and the Nikkiso HPM-15", Artificial Organs, 24 (11), pp. 889-892, 2000.

Y. Orime et al., "Clinical evaluation of the Gyro Pump Cle3 as a cardiopulmonary bypass pump", Asaio Journal 2000, 46, pp. 128-133.

Y. Orime et al., "Jostra Rota Flow RF-30 pump system: A new centrifugal blood pump for cardiopulmonary bypass", Artificial Organs, 24 (6), pp. 437-441, 2000.

A.M. Fallon et al., "Flow and thrombosis at orifices simulating mechanical heart valve leakage regions", Journal of Biomechanical Engineering-Transactions of the Asme, vol. 128, Feb. 2006, pp. 30-39.

D. Bluestein et al., "Steady flow in an aneurysm model: Correlation between fluid dynamics and blood platelet deposition", Journal of Biomechanical Engineering-Transactions of the Asme, vol. 118, Aug. 1996, pp. 280-286.

D. Arora et al., "A tensor-based measure for estimating blood damage", Artificial Organs, 28 (11), pp. 1002-1015, 2004.

(56) References Cited

OTHER PUBLICATIONS

M. Giersiepen et al., "Estimation of Shear Stress-Related Blood Damage in Heart-Valve Prosthesis—Invitro Comparison of 25 Aortic Valves", The International Journal of Artificial Organs, vol. 13, No. 5, pp. 300-306, 1990.

T. Spanier et al., "Activation of coagulation and fibrinolytic pathways in patients with left ventricular assist devices", Journal of Thoracic and Cardiovascular Surgery, vol. 112, No. 4, Oct. 1996, pp. 1090-1097.

J. Dale et al., "Intravascular Hemolysis in Late Course of Aortic-Valve Replacement—Relation to Valve Type, Size, and Function", American Heart Journal, vol. 96, No. 1, Jul. 1978, pp. 24-30.

T.C. Lamson et al., "Relative blood damage in the three phases of a prosthetic heart valve flow cycle", ASAIO Journal, vol. 39, pp. M626-M633, 1993.

N. Maugeri et al, "Circulating platelet/polymorphonuclear leukocyte mixed-cell aggregates in patients with mechanical heart valve replacement", American Journal of Hematology, 65, pp. 93-98, 2000.

J. Ansell et al., "Managing oral anticoagulant therapy", Sixth ACCP Consensus Conference on Antithrombotic Therapy, Chest, 119, pp. 22S-38S, 2001.

S.C. Cannegieter et al., "Optimal Oral Anticoagulant-Therapy in Patients with Mechanical Heart-Valves", New England Journal of Medicine, vol. 333, No. 1, pp. 11-17, 1995.

P.D. Stein et al., "Antithrombotic therapy in patients with mechanical and biological prosthetic heart valves", Sixth ACCP Consensus Conference on Antithrombotic Therapy, Chest / 119 / 1 / Jan. 2001 Supplement, pp. 220S-227S.

Felix J.M. vd Meer et al., "Bleeding Complications in Patients Treated with Oral Anticoagulants in a Routine Situation", Thrombosis and Haemostasis, 69 (6), Jun. 30, 1993, p. 982.

I.M. Whyte et al., "Acetaminophen causes an increased International Normalized Ratio by reducing functional factor VII", Therapeutic Drug Monitoring, 22, pp. 742-748, 2000.

D.M. Bushnell et al., "Turbulence Control in Wall Flows", Annual Review of Fluid Mechanics, 21, pp. 1-20, 1989.

W.L. Goodman, "Emmons Spot Forcing for Turbulent Drag Reduction", AIAA Journal, vol. 23, No. 1, Jan. 1985, pp. 155-157.

Y.G. Guezennec et al., "Mechanisms Leading to Net Drag Reduction in Manipulated Turbulent Boundary-Layers", AIAA Journal, vol. 28, No. 2, Feb. 1990, pp. 245-252.

P. Moin et al., "Tackling turbulence with supercomputers", Scientific American, vol. 276, No. 1, Jan. 1997, pp. 62-68.

L.J. Bradbury et al., "The Distortion of a Jet by Tabs", Journal of Fluid Mechanics, vol. 70, Part 4, pp. 801-813, 1975.

K. Ahuja et al., "Shear flow control by mechanical tables"., AIAA Journal, 89-0994, 10 pgs., 1989.

J. Ng et al., "Components for integrated poly(dimethysiloxane) microfluidic systems", Electrophoresis, 23, pp. 3461-3473, 2002.

S.R. Quake et al., "From micro- to nanofabrication with soft materials", Science, vol. 290, Nov. 2000, pp. 1536-1540.

C.G. Nevaril et al., "Erythrocyte Damage and Destruction Induced by Shearing Stress , Journal of Laboratory and Clinical Medicine", The Journal of Laboratory and Clinical Medicine, vol. 71, No. 5, May 1968, p. 784.

L.J. Wurzinger et al., "Mechanical blood trauma: an overview", Angeiologie, 38, Apr.3-May 1986,, pp. 81-97.

K. Ahuja et al., "Shear flow control by mechanical tables"., AIAA Journal, 89/0994, 10 pgs., 1989.

J. Ng et al., "Components for integrated poly(dimethysiloxane) microfluidic systems", Electrophoresis, 23, pp. 3461-3473,2002.

Simon, H.S.; *"Influence of the Implant Location on the Hinge and Leakage Flow Fields Through Bileaflet Mechanical Heart Valves"*; Chemical and Biomolecular Engineering Department, Georgia Institute of Technology; May 2004; 261 Pgs.

Travis, B.; *"The effects of Bileaflet Prosthesis Pivot Geometry on Turbulence and Blood Damage Potential"*; PhD Thesis, Chemical Engineering Department, Georgia Institute of Technology; Apr. 2001; 375 Pgs.

Fallon, A.M.; *"The Development of a Novel in vitro Flow System to Evaluate Platelet Activation and Procoagulant Potential Induced by Bileaflet Mechanical Heart Valve Leakage Jets"*; Chemical and Biomolecular Engineering Department, Georgia Institute of Technology; 2005, May 2006; 339 Pgs.

Leo, H.-L.; *"An In Vitro Investigation of the Flow Fields Through Bileaflet and Polymeric Prosthetic Heart Valves"*, Biomedical Engineering Department, Georgia Institute of Technology, Aug. 2005; 534 Pgs.

Harker et al.; *"Studies of Platelet and Fibrinogen Kentics in Patients with Prosthetic Heart Valves"*; New England Journal of Medicine, vol. 283, Dec. 10, 1970; pp. 1302-1305.

Leverett, L.B., Hellums, J.D., Alfrey, C.P., Lynch, E.C., *"Red Blood Cell Damage by Shear Stress"*; Biophysical Journal 1972;12(3):257-27; (17 pgs.).

Sutera, S.P.; *"Flow-induced trauma to blood cells"*; Circulation Research 1977;41(1):2-8; (8 pgs.).

European Office Communication dated Jun. 17, 2014 in Application No. 07 864 458.0, 4 pgs.

* cited by examiner

FLOW MANIPULATION IN BIOLOGICAL FLOWS USING VORTEX GENERATORS

I. CROSS-REFERENCE TO RELATED APPLICATIONS

The present application is related to U.S. provisional patent application having Ser. No. 60/865,919 titled "Flow Manipulation Devices for Prosthetic Heart Valves" filed Nov. 15, 2006 which is hereby incorporated by reference in its entirety and with priority of the present application being claimed to Nov. 15, 2006.

II. FIELD OF INVENTION

The present invention relates to systems and methods for manipulating biological flows. More particularly, the present invention relates to managing flow through medical devices to reduce risk of adverse events attributable to shear stress.

III. BACKGROUND OF THE INVENTION

It is well established that adverse events (such as blood element or cell damage, thrombus formation, and platelet activation) can be caused by flow-induced shear stresses. These factors may seriously limit the performance of a broad range of devices used to transport biological fluids. By way of non-limiting example, such devices include cardiovascular hardware, prosthetic valves, stents, bypass pumps, and flow-assist devices as well as conduits for transporting such fluids. In particular, there exists a large body of scientific literature that has emphasized the significant risk associated when blood elements are subjected to non-physiological hemodynamic shear stresses in in-vivo devices (heart valves, flow assist devices etc.), and the severe limitations of non in-vivo devices (bypass pumps, dialysis machines, heart-lung instruments, or syringe needles, etc.).

Implanted ventricular assist devices (VADs) have also been implicated in thromboembolic events. Other known examples of blood damage in cardiovascular systems include centrifugal blood pumps that are used during bypass surgery and have been shown to cause hemolysis and platelet activation, which can lead to thromboembolism. Also, blood flow over surfaces of vascular stents (coronary or peripheral stents) can induce shear stress resulting in thrombus formation.

Shear stress can lead to coagulation and thromboemboli formation by either damaging the red blood cell (RBC) or by mechanically activating the platelet. High levels of shear stress can tear the RBC membrane, thus exposing tissue factor to the plasma and initiating the tissue factor pathway of the coagulation cascade. Shear stress can also trigger the coagulation cascade by activating platelets directly. Platelets are activated by shear stress that results in mechanotransduction of the force to a GP1b receptor.

This mechanotransduction enables binding of the GP1b receptor to Von Willebrand Factor (vWF) and a subsequent influx of calcium ions, resulting in platelet activation. Upon activations the GpIIb/IIIa receptor is activated and can then bind to other ligands such as fibrinogen, vWF, fibronectin, and vitronectin. The coagulation cascade is propagated and can lead to the formation of thrombin-anti-thrombin III (TAT), which is a relative measure of thrombin formation. RBCs are vulnerable to sub-lethal damage at shear stresses of 500 dynes/cm$^2$ and by as little as 10-100 dynes/cm$^2$ in the presence of foreign surfaces. In addition, platelet activation can occur at shear stresses as low as 60-80 dynes/cm$^2$.

Flow stasis and recirculation regions have been shown to correlate to platelet deposition, particularly if these regions directly follow after a high shear stress region. The flow stagnation regions that occur at the blood-material interface on cardiovascular devices immediately adjacent to these high shear stress flow environments can promote damaged blood elements deposition, leading to thrombus formation on the cardiovascular devices.

Another important factor affecting the degree of blood damage is the amount of time the blood element spends in the high shear stress region. Shear-induced platelet activation and hemolysis are known to be a result of extended exposure of blood cells to high levels of shear stress. Previous studies have emphasized the importance of both stress magnitude and exposure time as important parameters in assessing shear related blood cell damage. The closing flow transients that occur during the leaflet closure phase are associated with the formation of a strong leakage jet in the B-datum region preceded by strong counter rotating starting vortices of high shear rates.

There exists a need for systems and methods for flow control devices that can minimize the magnitude of shear stresses experienced by blood elements. The flow control devices should counteract the formation of strong vortices thereby reducing the overall platelet activation potential of cardiovascular devices. In addition, the flow control devices should mitigate the adverse effects of high shear stress in blood-contacting devices and manipulate secondary vorticity concentrations within the blood flow. Furthermore, the flow control devices should enhance cross stream mixing and momentum transfer to diminish local velocity gradients and corresponding shear stress distributions.

IV. SUMMARY OF THE INVENTION

The present application discloses various devices for use in combination with a fluid flow having a biologic component and subject to an adverse response to shear stress. The device includes a surface in contact with the flow of the fluid. The surface has a longitudinal direction extending from a leading end toward a trailing end and aligned with a direction of the flow. The device is susceptible to fluid flow phenomena including boundary layer formation within the flow sufficient for a resulting shear stress to induce the thrombogenic response, or free shear flow formation such as jet, separation zones of sufficient characteristic to induce the thrombogenic response. The surface includes a surface feature sufficient to alter the fluid flow such as to reduce the overall shear stress that the biologic components may encounter while transiting through the device.

In addition, aspects of the present invention include an implant for chronic placement in a patient's body. The implant has a lumen defining a blood flow path for a blood flow having flow characteristics including a flow rate. The implant has a surface at least partially defining the lumen and in contact with the blood flow. The surface has a longitudinal direction extending from a leading end toward a trailing end. In addition, the device is susceptible to fluid flow phenomena including boundary layer formation within the flow sufficient for a resulting shear stress to induce the response, or free shear flow formation such as jet, separation zones of sufficient characteristic to induce the thrombogenic response. The surface includes a surface feature sufficient to alter the fluid flow such as to reduce the overall shear stress that the blood may encounter while transiting through the device.

Furthermore, the present invention includes examples of a device for receiving blood from a patient, treating the blood and returning the treated blood to the patient. The device comprises a plurality of blood flow pathways for containing and directing a blood flow. The blood flow has flow characteristics including a flow rate. At least one of said pathways has a surface at least partially defining the pathway and in contact with the blood flow. The surface has a longitudinal direction extending from a leading end toward a trailing end and the surface is susceptible to inducing boundary layer formation, jet formation, or flow separation within the blood flow. The surface has characteristics sufficient to induce a thrombogenic response. Furthermore, the surface includes a surface feature sufficient to alter the blood flow such as to reduce the overall shear stress that the blood may encounter while transiting through the device.

V. BRIEF DESCRIPTION OF THE DRAWINGS

Non-limiting and non-exhaustive embodiments are described with reference to the following figures, wherein like reference numerals refer to like parts throughout the various views unless otherwise specified.

VI. DETAILED DESCRIPTION OF A PREFERRED EMBODIMENT

Various embodiments are described more fully below with reference to the accompanying drawings, which form a part hereof, and which show specific embodiments of the invention. However, embodiments may be implemented in many different forms and should not be construed as limited to the embodiments set forth herein; rather, these embodiments are provided so that this disclosure will be thorough and complete, and will fully convey the scope of the invention to those skilled in the art. Accordingly, the following detailed description is, therefore, not to be taken in a limiting sense. Note that throughout this specification, protrusion, protuberance, surface irregularity, surface indentation, and vortex generator may be used interchangeably.

The present invention will be described in a preferred embodiment of passive surface modifications to avoid excessive shear stress in devices in contact with blood flow. Such devices may be chronically implanted devices (e.g., LVAD's, stents, valves, etc.) or may be external devices (e.g., blood pumps, blood oxygenators, etc.) or may be blood conduits (e.g., catheters). Further, while use in blood flow is a currently most preferred embodiment, the present invention is applicable to biological fluids in general (including therapeutic fluids such as therapeutic agents such as cell components, drugs or the like administered in an aqueous medium).

Figure 1:
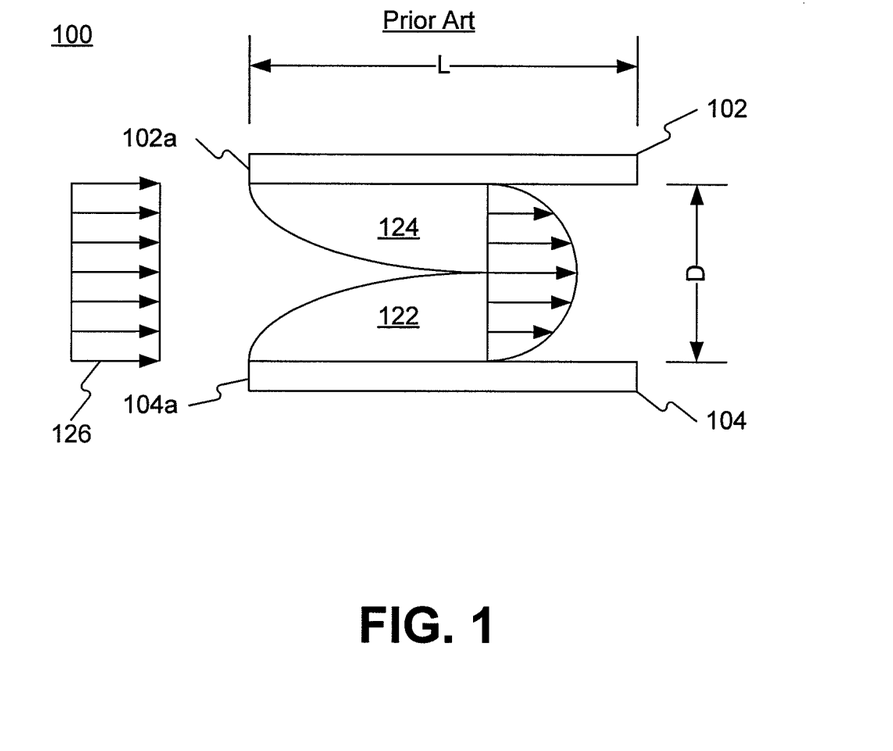
FIG. 1 is a schematic representation of a prior art device having surfaces in chronic contact with a patient's blood flow and having no passive means for reducing shear stress in the flow.

FIG. 1 illustrates a prior art device 100 with a surface in contact with a patient's blood flow. The device 100 includes walls 102 and 104. As blood flows through the device 100, a bulk flow 126 contacts the device 100 at the leading edges 102a, 104a of walls 102 and 104. As the bulk flow 126 flows through the device 100, boundary layers 122 and 124 may form in the entrance region of the device 100. Depending upon the length ("L") and diameter ("D") of the device 100, fully developed flow may or may not develop. Boundary layers 122 and 124 cause shear stresses to develop along walls 102 and 104.

Figure 2:
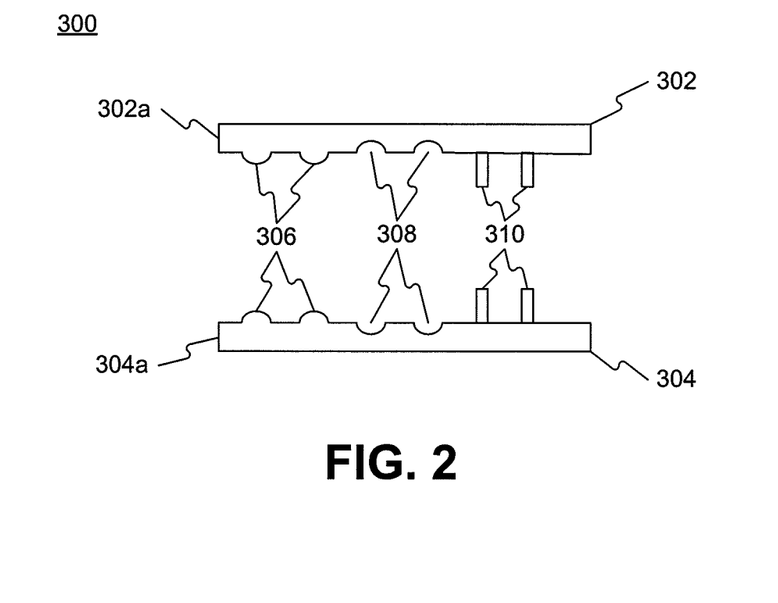
FIG. 2 is a schematic representation of the device of FIG. 1 modified according to the present invention.
Figure 3:
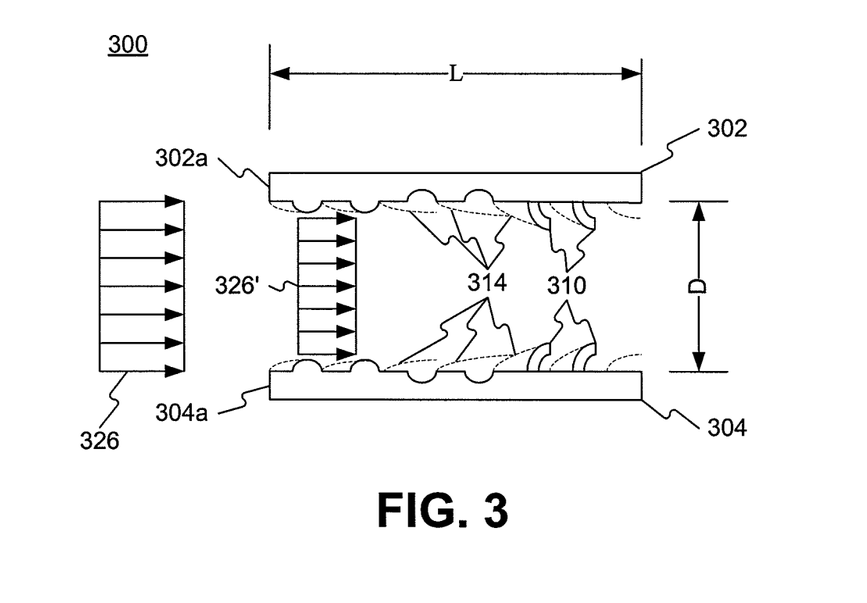
FIG. 3 is the view of FIG. 2 illustrating flow response to the modification of the present invention.

Referring now to FIGS. 2 and 3, a schematic representation of a device 300 according to various aspects of the present invention is shown. Device 300 includes surfaces 302 and 304 having various vortex generators 206, 208, and 110 spaced from leading edges 302a and 304a along a flow direction (indicated by the arrows in FIG. 3). Note that while FIGS. 2 and 3 show three different types of vortex generators depicted on surfaces 302 and 304 it is contemplated that a single type of vortex generator or two or more vortex generators may be implemented on device 300.

Vortex generators 306, 308, and 310 may be characterized by characteristics including but not limited to angle of attack, height, depth, flexibility, and spacing sufficient to create a region of vortex formation proximate vortex generators 306, 308, and 310. It will be appreciated that selection of such characteristics for a given flow characteristic (such as flow rate) is well within the skill level of one of ordinary skill in the art having the benefit of the present disclosure.

Vortex generators 306, 308, and 310 may induce the formation of secondary counter-rotating streamwise vortex pairs 314 which interact with the shear layer and induce cross stream mixing. This cross-stream mixing leads to broadening of the jet stream and to dissipation of small-scale motions.

In various aspects of the invention, vortex generators such as vortex generators 310 may be conformable. The interest in conformable flow control elements stems from the fact that they may be designed to adapt their functionality to the cyclical state of the embedding flow during a cardiac cycle. For example, vortex generators that are highly effective for reducing blood damage during valve closure may be pushed out of the way (e.g., bend towards the surface) when the embedding flow reverses its direction to minimize losses. Alternatively, the flexible flow control devices may be reconfigured and have different functionality to beneficially affect the reverse. In addition, the functionality of the passive devices can be potentially enhanced by allowing them to interactively oscillate as they shed streamwise vorticity.

Figure 12:
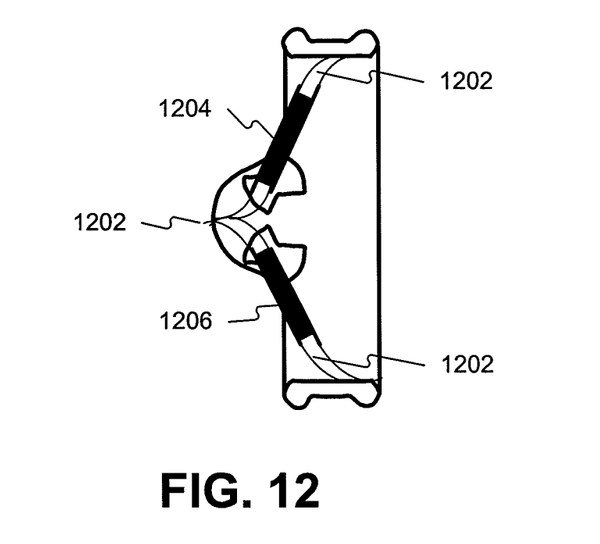
FIG. 12 depicts a bileaflet heart valve having flexible tips.

FIG. 12 shows an implementation of flexible tip passive flow control on the contemporary rigid bileaflet heart valve 1200 comprising flexible tips 1202 and leaflets 1204 and 1206. Flexible tips 1202 help ensure smooth closing of heart valve 1200 thus eliminating the typical colliding, nature of leaflets 1204 and 1206 closure. The closure has been attributed to formation of extreme pressure gradients that lead to cavitation and hemolysis. Flexible tips 1202 help ensure that the added compliance at the contact points provide a smooth contact as well as a damping effect to eliminate the water hammer effect. Additionally, it is anticipated that flexible lips 1202 may greatly reduce leakage through a b-datum and peripheral gaps during a cardiac cycle's leakage phase.

Protuberance or other surface irregularities may be rigid flow control elements. In addition to being rigid, protuberance or other surface irregularities may be flexible passive flow control elements. The use of flexible elements for flow control is attractive because it offers expanded control authority. The interest in conformable flow control elements stems from the fact that they can be designed to adapt their functionality to the cyclical state of the embedding flow during a flow cycle. For example, vortex generators that are highly effective for reducing blood damage during valve closure can be pushed out of the way (e.g., bend towards the surface) when the embedding flow reverses its direction to minimize losses. In addition, the flexible flow control devices can be reconfigured and have different functionality to beneficially affect the reverse. In addition, the functionality of the passive devices can be potentially enhanced by allowing them to interactively oscillate as they shed streamwise vorticity.

The angle of attack, height, depth, and spacing of vortex generators 306, 308, and 310 are great enough to retard boundary layer formation thereby reducing shear stress at surfaces 302 and 304. The internal blood flow within device 300 is shown at 326' and the approaching flow is shown at 326. In addition, the height and spacing of vortex generators 306, 308, and 310 are small enough to discourage flow stagnation (e.g. pooling, clotting, and clumping of the flow) proximate vortex generators 306, 308, and 310. Again, determination of specifics of such features for a given flow is within the skill level of one of ordinary skill in the art having the benefit of the teachings of the present invention. Also, note that vortex generators 306, 308, and 310 can be at arbitrary angles to surfaces 302 and 304 and the flow. In addition, the angle relative to surfaces 302 and 304 may be device specific.

The height and spacing of vortex generators 306 and 310 are such that vortex generators 306 and 310 do not substantially reduce a cross-sectional area in the flow direction or volumetric flow rate through device 300. Characterization of a substantial reduction in the cross-sectional area or volumetric flow rate may be a noticeable reduction in blood flow to the point that the effective diameter or other characteristic length associated with measuring the cross-sectional area or volumetric flow rate is reduced. For example, if vortex generators 306 and 310 reduce the cross-sectional area by 10-15%, this may constitute a substantial reduction in the cross-sectional area. Another example may be that if vortex generators 306 and 310 reduce the volumetric flow rate to the point vortex generators 306 and 310 simulate coronary artery plaque or other artery blockage, this may constitute a substantial reduction in the volumetric flow rate.

Note that depending on the flow (i.e. the material flow, flow speed, overall cross-sectional area, hydraulic diameter. Reynolds Number (Re), Euler Number (Eu), etc.) a reduction in the cross-sectional area by 10-15% does not necessarily translate to increased energy losses (i.e. a substantial reduction in the cross-section area). A decrease in overall shear stress experienced by the fluid translates to lower drag and lesser energy losses.

As described above, embodiments of the present invention utilize passive flow control devices for manipulating and controlling the evolution of both free and wall-bounded turbulent shear flows. Passive flow control devices may have morphology and structural features to alter the flow over the device's surface and active flow control (e.g., movable fins or other movable protuberances) to achieve drag reduction, thrust production, and propulsive efficiency. These devices generally use distributed element arrays (e.g. surface irregularities) that may protrude above the surface or indentations or grooves that penetrate into the device's surface.

Figure 11:
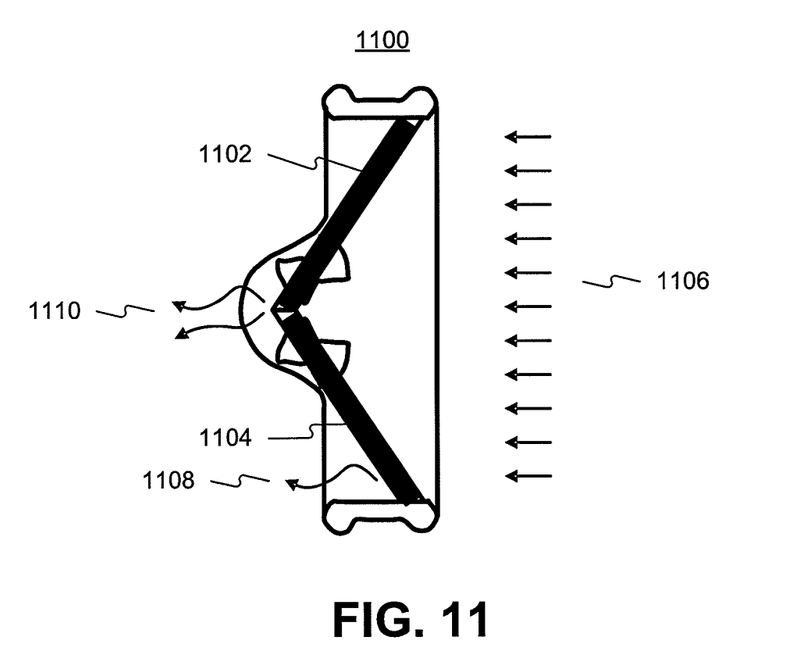
FIG. 11 depicts a bileaflet heart valve experiencing leakage.

Vortex generators that protrude from the surface may include transverse cylinders, plates, and airfoils that may be oriented parallel or normal to the flow and within the boundary layer or shear layer or any other location where there is fairly strong shear within the flow. In the parallel configuration these plates or airfoils may shed transverse (i.e. spanwise) vortices along the device and may lead to the wall boundary layer prematurely transitioning to turbulent flow (i.e. boundary layer "tripping"), turbulent flow structure modification, or may break up larger vortical eddies that are present in the flow. The plates or airfoils (i.e. surface irregularity) may act as mixers to facilitate avoidance of regions where the shear may be strong. This may be done by forcing flow from either slow moving fluid to rapid, fast moving fluid or forcing flow from fast moving fluid into slow moving fluid. By forcing flow from slow moving fluid to fast moving fluid the velocity may equalize, (i.e. the overall velocity gradient may become smaller). In addition to altering boundary layer formation, the vortex generators may also alter free shear flows that are generated by the device (e.g. leakage jets, shear layers etc.). For instance, a heart valve 1100 may comprises leaflets 1102 and 1104. As a flow 1106 flows through heart valve 1100, the can be hinge leakage 1108 and leakage jet 1110 formation.

Low-aspect ratio (i.e., short span) plates and airfoils that are mounted normal to the surface along their (long) chords are called vortex generators. Because the vortex generators are mounted at an angle of attack relative to the oncoming flow, they form either clockwise or counterclockwise (depending on their orientation) "wing tip" streamwise vortices. The vortex generators are typically arranged in spanwise arrays that can be formed with single (same orientation) or symmetric pairs to produce either single-sign or counter rotating streamwise vortex pairs.

Vortices scale with the characteristic dimensions of the generating elements and lead to enhancement of entrainment (e.g., transfer of high-momentum fluid towards the surface) and small-scale fluid mixing within the embedding flow field. In external and internal flows, flow separation suppression or mitigation and mixing enhancement within free shear flows are typically dominated by large coherent vortical structures. Flow control devices that are embedded in the flow surface include dimples, riblets, and small-scale streamwise grooves that can reduce turbulent skin friction. These riblets break up spanwise vortices and reduce the surface shear stress and momentum loss by preventing eddies from transporting high speed fluid close to the surface.

Free turbulent jets demonstrate that the interaction between the jet's predominantly azimuthal vorticity and the streamwise vortices induced by passive vortex generators can lead to mixing enhancement and therefore to reduction in shear. Moreover, the increase in small-scale motion within the flow leads to enhancement and consequently to dissipation of turbulent fluctuations.

Axial vorticity may be introduced by placing tabs at the jet exit such that they protruded into the flow with an area blockage of approximately 1-2% per tab. As little as two tabs may significantly increase mixing sufficiently to reduce the potential core length and increase the decay of the centerline velocity. This increased mixing and decay may increase jet spreading and reduce the flow shear. Streamwise vorticity generation at the jet exit may be promoted by enforcing azimuthal excitation through vortex generators or tabs at the edge of the nozzle or by using corrugated, lobed, or indented nozzle edges.

As described above, surface irregularities or vortex generators may be placed in any type of device used to transport biological materials or materials susceptible to damage where there may be increased shear levels that may lead to damage due to flow separation internally or bifurcation within the device. For example, vortex generators may be used in cardiovascular device to reduce shear levels that may lead to blood damaged due to flow separation or bifurcation within blood vessels. The flow separation and bifurcation may cause separation and recirculation that may also lead to damage of the flow material.

The passive vortex generators may be fabricated using molding technologies and bio-compatible polymeric materials (e.g., PDMS). As noted above, the elasticity and other mechanical properties of the molding material may be selected so that the fins can bend appreciably (and therefore minimize their cross stream protrusion) when the flow over the leaflets reversed direction.

Passive flow control devices can be effectively realized using advanced fabrication technologies. In particular, soft polymers (e.g., PDMS) that are biocompatible can be adapted for the fabrication of intricate surface devices using a combination of rapid prototyping (e.g. solid object printing) and soft lithography. Moreover, these elastomers can be fabricated in submicron features with no discernible pattern degradation or surface distortion. Submicron resolution molds can be generated by electron beam lithography, for example, to yield nano-scale patterns in replica molded elastomers. The effectiveness of surface integrable flow control devices may facilitate their implementation using new, nano-and microfabrication technologies may allow custom-fitting these devices to specific patients.

Figures 4, 4A:
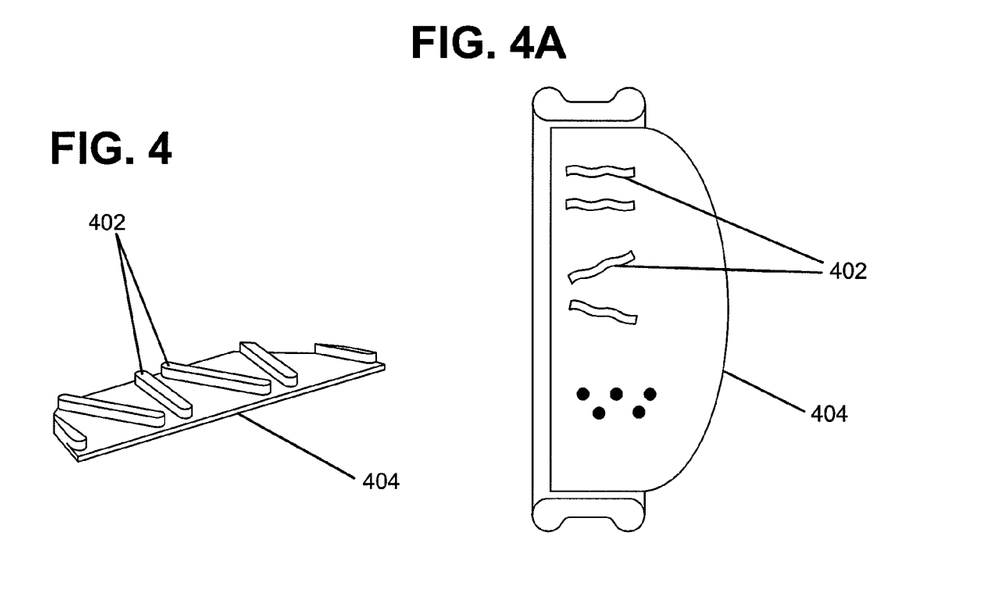
FIGS. 4 and 4A depict planer protuberances consistent with embodiments of the invention.
Figure 5:
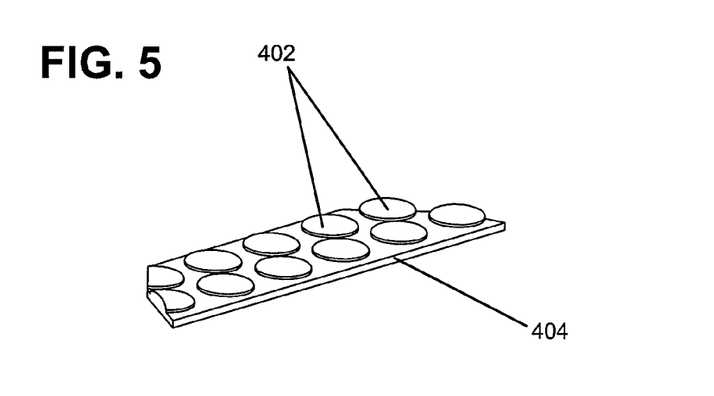
FIG. 5 depicts hemispherical protuberances consistent with embodiments of the invention.

Referring now to FIGS. 4 and 5, vortex generators 206 and 210 may be substantially planer (FIG. 4), substantially hemispherical (FIG. 5), a combination of substantially planer and substantially hemispherical shapes, serrated edges either in or normal to the plane of the leaflet, etc. Planar protuberances (e.g. rectangular vortex generators) consisted of rectangular fins 402. Each fin may produce a streamwise (wingtip) vortex where the sense of the vorticity (i.e., clockwise or counter clockwise) may depend on the angle of the fins 402 relative to a free stream. For example, consistent with embodiments of the present invention, each fin 402 may be 1 mm high (a base 0.5 mm thick) and may have an angle of attack of ±15° degrees relative to an oncoming flow. In other aspects of the invention, protuberance may be based on an array of staggered hemispherical protuberances 502. For example, hemispherical protuberances 502 may have a diameter of 1 mm with an edge to edge spacing of 0.5 mm. In addition, while FIGS. 4 and 5 show the protuberances substantially parallel (FIG. 4) and substantially perpendicular (FIG. 5) to the blood flow direction, it is contemplated that the protuberances may be parallel, perpendicular, or a combination of both to blood flow direction.

Figure 6:
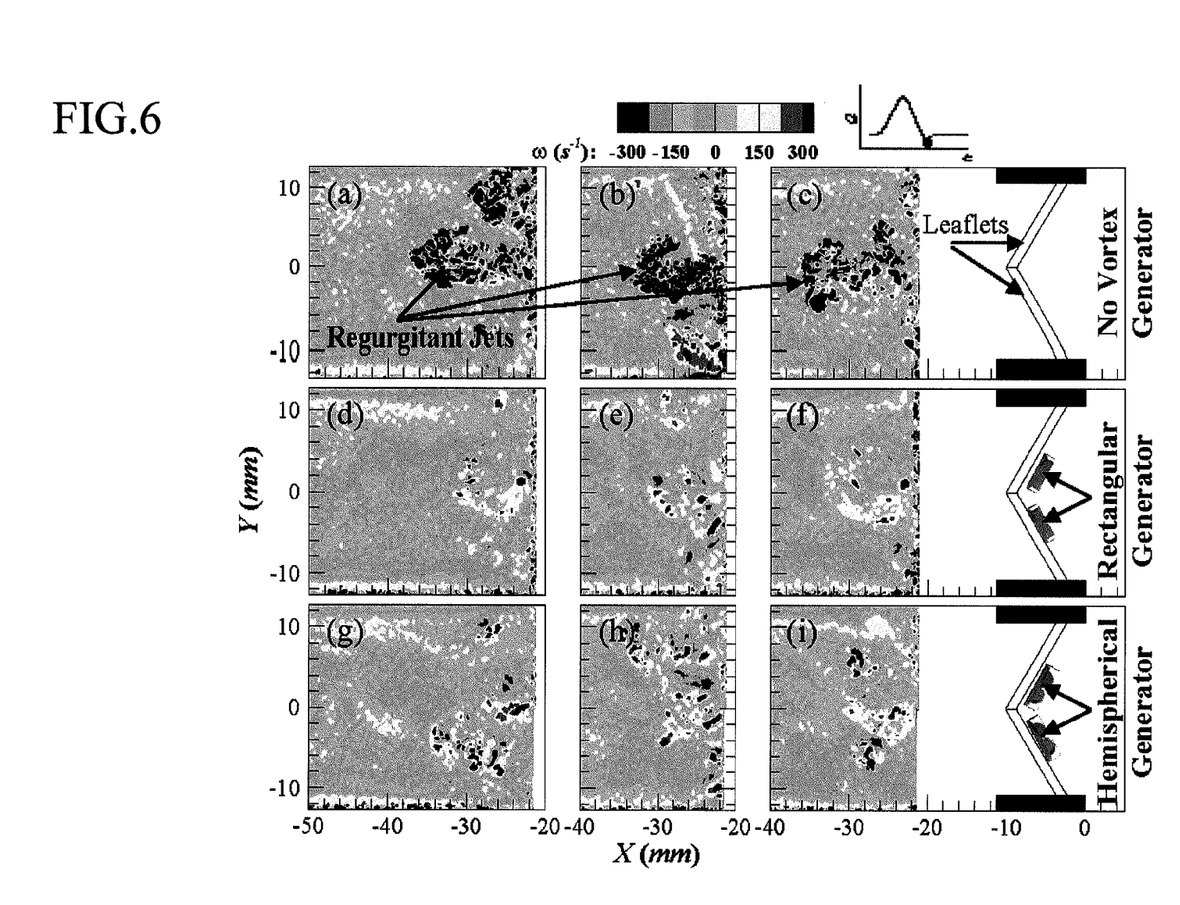
FIG. 6 depicts maps of instantaneous vorticity fields at the moment of valve closure.

Referring now to FIG. 6, FIG. 6 depicts maps of instantaneous vorticity fields at the moment of valve closure. The flow characteristics of the transitory jet and the influence of vortex generators were investigated using high resolution particle image velocimetry (PIV). The plane of measurement was aligned along the centerplane of the chamber and perpendicular to the leaflet axis. The measurements were phase locked such that the velocity field was captured throughout the cardiac cycle of 860 ms with 20 ms increments. The vorticity fields capture regurgitant jets for a heart valve having no vortex generators, rectangular or planer vortex generators, and hemispherical vortex generator.

The small-scale vorticity concentrations associated with the strong momentary jet are clearly visible in the three PIV "snapshots". These vorticity distributions indicate the presence of high-shear flow domains that are advected with the jet flow.

The sample PIV snapshots in FIG. 6 show the remarkable impact of the vortex generators on the momentary jet flow. For both planer and hemispherical vortex generator arrays, the jet becomes highly diffused and well mixed as may be concluded from the structure of the voracity concentrations which are very weak. It is also interesting to note that at least by the measure of the vorticity concentrations, the rectangular vortex generators appear to be more effective than the hemispherical generators.

Ensemble-averaged distributions of the Reynolds stresses for the three configurations of FIG. 6 (shown in FIG. 7) confirms that the passive vortex generators strongly reduce the magnitude of the turbulent fluctuations within the flow owing to increased dissipation. The PIV measurements indicate that the vortex generators have a strong effect on the jet flow field. The mean velocity distributions (FIG. 7) indicate that in the presence of the vortex generators the shear layers of the jet are significantly narrower owing to increased mixing along the jet's edges and that the core of the jet is moving a faster.

Figure 7:
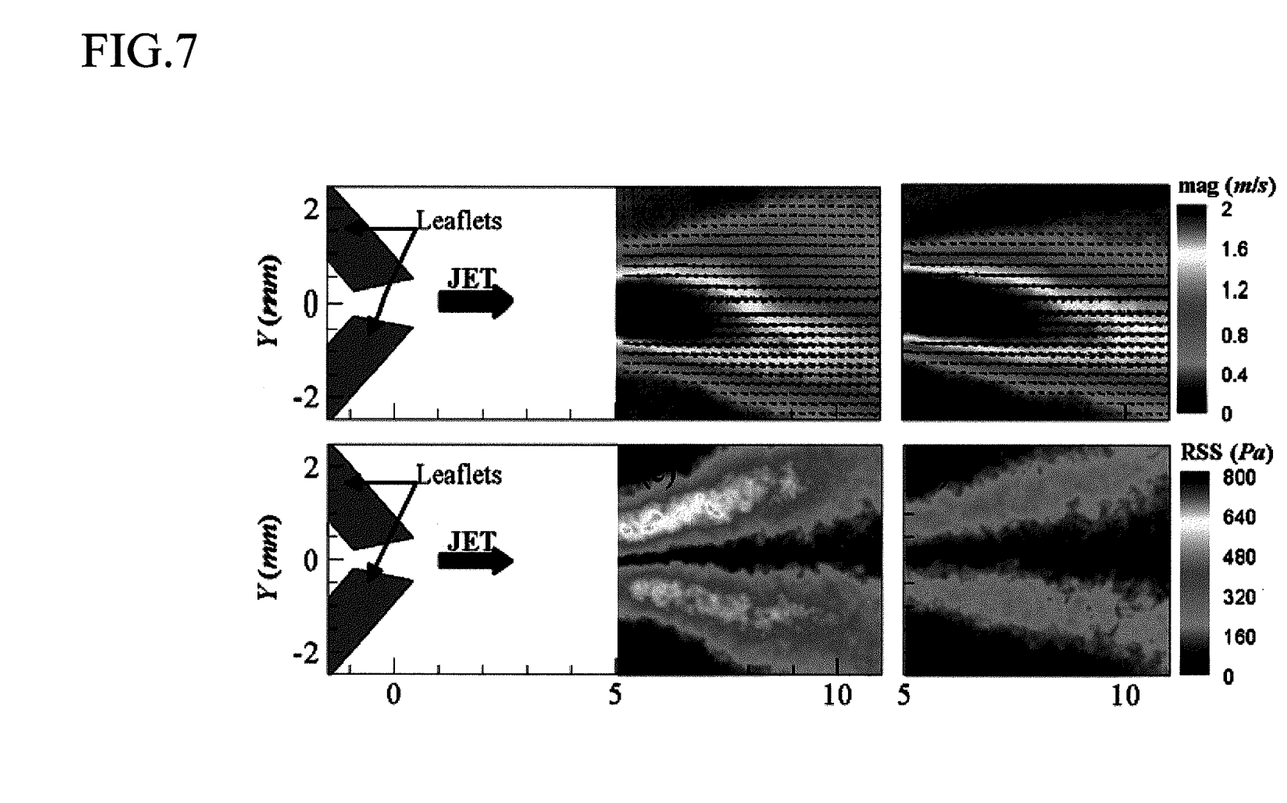
FIG. 7 depict contour plots of mean velocity for the steady b-datum jet from the valve without and with rectangular vortex generators and Reynolds shear stress for the steady b-datum jet from the valve without and with rectangular vortex generators.

The strong impact of the passive vortex generators on the evolution of the jet flow may be discerned from distributions of the Reynolds stresses (FIG. 7). This data shows a strong reduction in the magnitude of the velocity fluctuations within the jet and therefore in the instantaneous mechanical shear to which the blood cells are subjected. The data show that the Reynolds stresses decrease by (nominally) 50%.

As discussed above, TAT is an established measure to access the pro-coagulant potential of various valves. In order to confirm that the changes in the flow induced by the vortex generators also alter the pro-coagulant nature of the valve, a series of measurements were conducted in vitro. Heart valves with and without vortex generators were tested in a flow loop to measure the TAT concentration in blood over a period of one hour at 15 min intervals.

Figure 8:
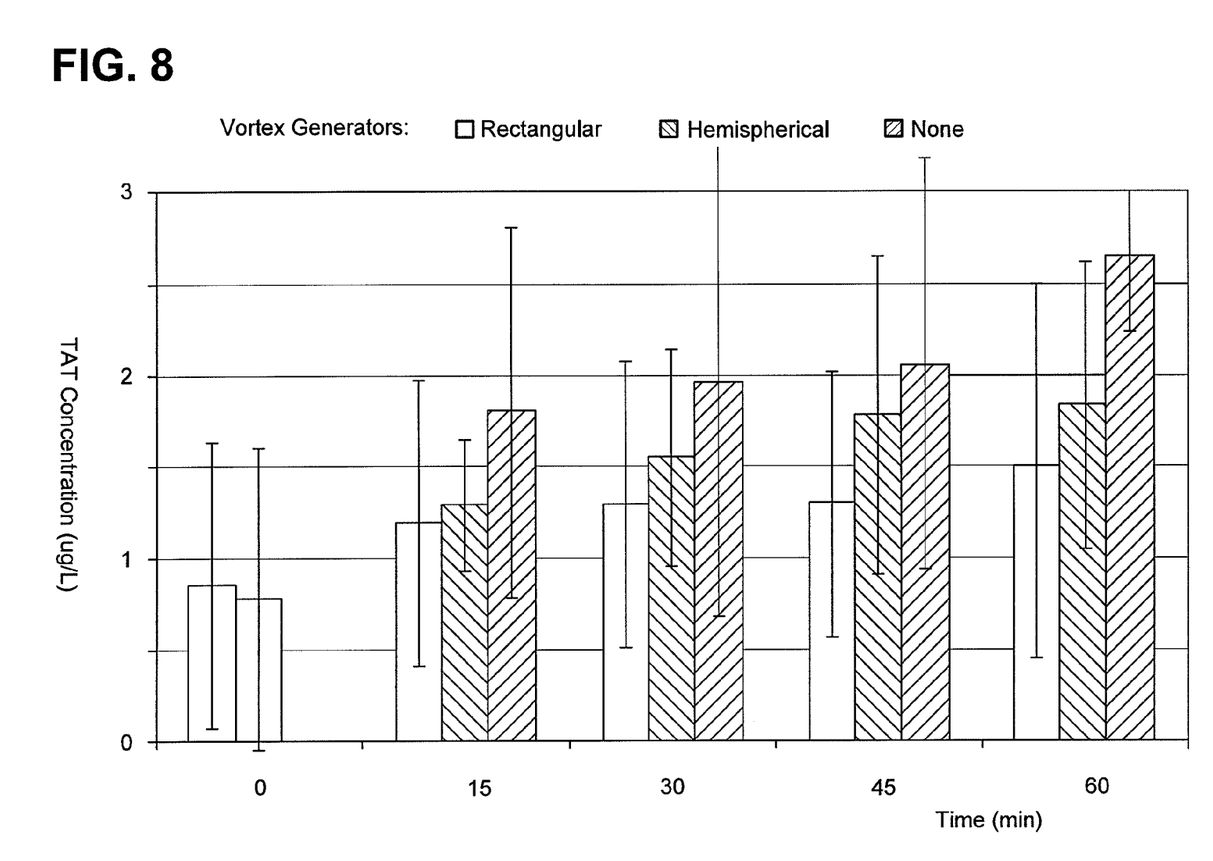
FIG. 8 depicts comparison of TAT concentration with and without vortex generators.

FIG. 8 depicts a comparison of TAT measurements (taken at 15 min intervals) in the three configurations considered here (i.e. the baseline valve, and in the presence of rectangular and hemispherical vortex generators). This data clearly show that TAT concentration increases steadily with time for all three cases indicating a gradual progress in overall blood coagulation levels in the system. However, the total TAT concentration in the presence of the vortex generators is substantially lower than in the baseline valve. In particular, the presence of the rectangular vortex generators leads to a 42% decrease in TAT concentration compared to the baseline. The production rate with the hemispherical vortex generators is higher than with the rectangular generators, but still significantly lower than in the absence of passive flow control (baseline). The significance of these results is underscored by the fact that they actually provide conservative estimates of the reduction in blood damage and that in reality these effects may be considerably higher. This is due to background blood damage and activation that are caused by other components in the loop such as the pump, loop fittings etc.

Embodiments of the present invention may be utilized on mechanical heart valves and other replacement cardiovascular devices that are rigid. In addition, embodiments of the present invention may be utilized on replacement cardiovascular devices and other devices in chronic contact with blood flow that are flexible and mimic real physiological heart valves, arteries and physiological structures. The use of flexible elements (e.g. surface edges and vortex generators) for cardiovascular flow control offers expanded control authority coupled with advanced, batch fabrication technologies.

The integration of vortex generators on material used to manufacture cardiovascular or other devices may be accomplished while still using bio-compatible materials such as PDMS that can be molded easily and quickly. Even when rigid cardiovascular devices are used, flexible materials may be integrated to form vortex generators. For example, one complaint of current heart valves does not have anything to do with the physiological applications but with "clicking". During opening and closing of the heart valve the metallic edges of the leaflets strike one another producing a clicking noise. In various aspects of the invention, a device may integrate a flexible material with hard/rigid materials during manufacturing to create soft tips at the edges to eliminate the clicking noise commonly associated with purely metallic heart valves. For instance, the edges of hear valve leaflets may be a flexible material, (i.e. a quiet material) and a majority of the leaflet surface could be rigid (See FIG. 12).

During manufacturing vortex generators may be molded into soft and rigid materials. Molding the vortex generators into the materials may eliminate the need to separately glue them onto the surface. For example, an implantable medical device could be molded out of flexible materials like PDMS. PDMS elastomer can conform to extremely small (submicron) features with no discernible pattern degradation or surface distortion. Moreover, these fabrication technologies suggest themselves as viable vehicles for realizing passive flow control devices in cardiovascular systems because soft polymers such as PDMS are stable, non-toxic, low-cost, with appealing physical and chemical properties that are also bio- and micro-fabrication compatible. Furthermore, some of these materials can be selected to have desirable properties such as optical transparency, tunable surface chemistry, thermal stability, good bonding characteristics, elasticity, high-gas, and low-water permeability.

Currently, a patient is measured for a prosthetic device and after manufacturing, the device is implanted. This can lead to problems in that the measurements may be taken via ultrasound technology and at best are estimates of the size needs. Many biocompatible materials can be molded quickly allowing for cardiovascular devices to be manufactured using, rapid prototyping technologies. Using rapid prototyping technologies and a surgeon may, in real time, manufacture a replacement cardiovascular device while the patient is on the operating table. For instance, after opening the patient's chest cavity the surgeon may measure the patient's heart directly. Once the direct measurements are taken, the actual machines necessary to manufacture a device (e.g. heart valve, replacement artery, stent) may be in the operating room and the replacement device fabricated in real time using direct measurements, not ultra sound measurements.

The passive vortex generators may be fabricated using molding technologies and biocompatible polymeric materials (e.g., PDMS). An aspect of the flexible vortex generators is the ability to prescribe the mechanical properties of the material and therefore the relaxation time following the change in flow direction. For example, the relaxation time can be scaled to optimize performance such that the vortex generators are fully extended only when the transitory jet reaches its full speed (i.e., before the valve closes completely).

Figure 9:
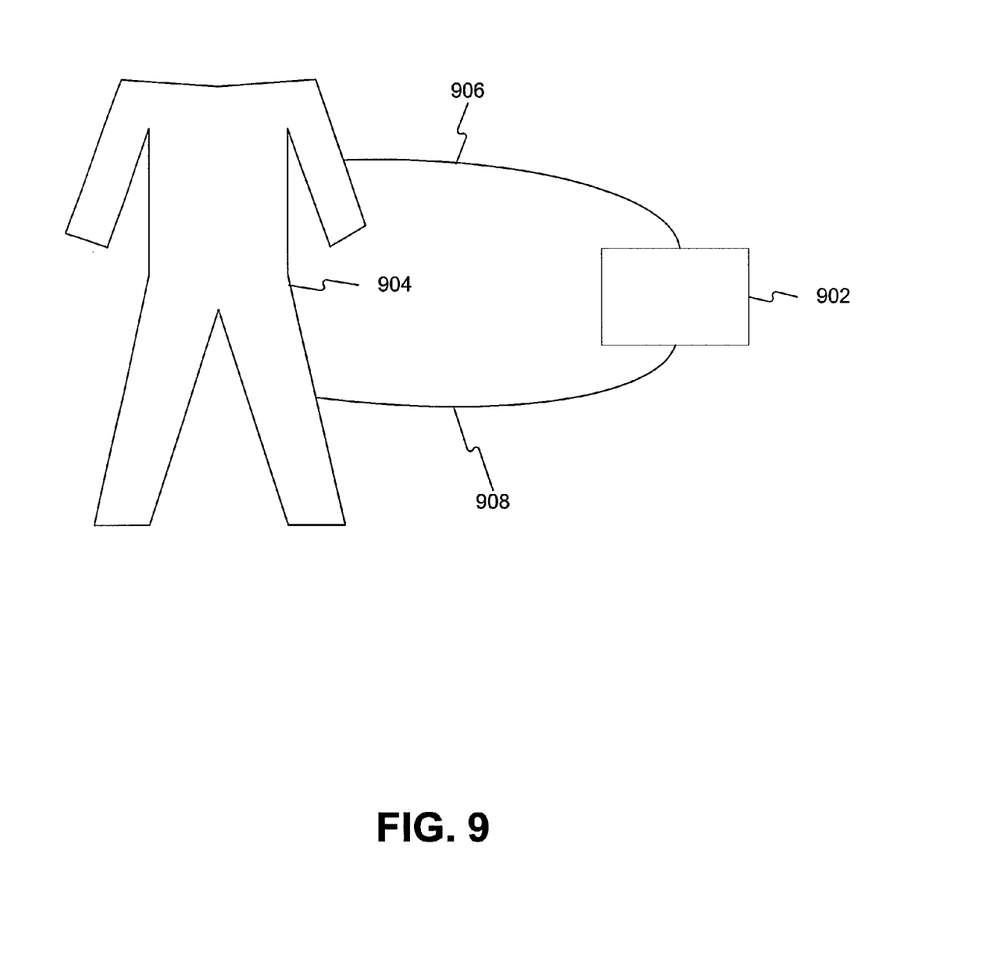
FIG. 9 depicts shows a situation where embodiments of the present invention may be employed on a device external to a patient.

FIG. 9 schematically illustrates the present invention employed on a device 902 external to a patient 904. For example, FIG. 9 shows device 902 connected to patient 904 via conduits 906 and 908. Any number of components within device 902 (or conduits 906, 908) may be fitted with vortex generators in efforts to minimize damage to biological fluids. For instance, device 902 may be a blood pump used during heart surgery. Piping within device 902 may be fitted with vortex generators as well as facets of other internal components. In addition, conduits 906 and 908 may also be fitted will vortex generators to minimize damage to biological fluids. By way of non-limiting example, device 902 may include: blood pumps, blood oxygenators, dialysis machines, drug delivery machines, syringes, etc.

While FIG. 9 has been described where device 902 receives biological fluids from patient 904 and then returns biological fluids to patient 902, it is contemplated that device 902 may only receive biological fluids from patient 904. For instance, device 902 may be any device used by agencies such as the RED CROSS during blood drives, or devices used by physicians do collect biological samples such as tissue and urine from patients. In addition, it is further contemplated that device 902 may only supply biological fluids to patient 904. For example, device 902 may be a device used during chemotherapy to deliver cells, drugs, blood, or other medical and biological elements to patient 904.

Figure 10:
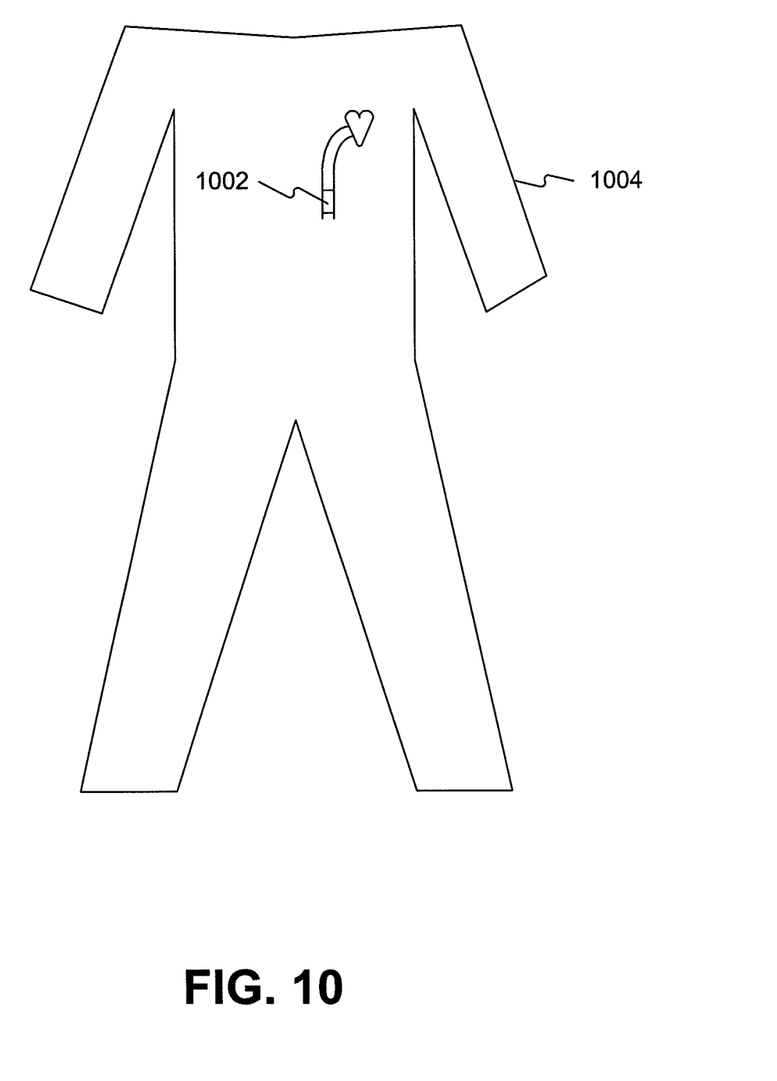
FIG. 10 depicts a situation where embodiments of the present invention may be deployed on a device internal to the patient.

FIG. 10 shows the present invention employed on a device 1002 internal to a patient 1004. For example, FIG. 10 shows device 1002 implanted into patient 1004. If device 1002 contains multiple components or facets, any number of device 1002's components or facets may be fitted with vortex generators in efforts to minimize damage to biological fluids. For instance, device 1002 may be a stent used to prop open an artery and the stent's facets may be fitted with surface protrusions and surface indentations to minimize damage to blood flowing though the stent. By way of example and not limitation, device 1002 may include heart valves, stents, LVAD's, etc.

In other instances, vortex generators may be utilized in systems where flow through the system may experience a discontinuity (e.g. between two different size pipes or tubes) giving rise to a velocity jump as the flow goes from the large diameter tube to a small diameter tube or vice versa. Surface irregularities may be used to help mitigate the effects of any sudden changes in velocity.

Reference may be made throughout this specification to "one embodiment," "an embodiment," "embodiments," "an aspect," or "aspects" meaning that a particular described feature, structure, or characteristic may be included in at least one embodiment of the present invention. Thus, usage of such phrases may refer to more than just one embodiment or aspect. In addition, the described features, structures, or characteristics may be combined in any suitable manner in one or more embodiments or aspects. Furthermore, reference to a single item may mean a single item or a plurality of items, just as reference to a plurality of items may mean a single item. Moreover, use of the term "and" when incorporated into a list is intended to imply that all the elements of the list, a single item of the list, or any combination of items in the list has been contemplated.

One skilled in the relevant art may recognize, however, that the invention may be practiced without one or more of the specific details, or with other methods, resources, materials, etc. In other instances, well known structures, resources, or operations have not been shown or described in detail merely to avoid obscuring aspects of the invention.

While example embodiments and applications of the present invention have been illustrated and described, it is to be understood that the invention is not limited to the precise configuration and resources described above. Various modifications, changes, and variations apparent to those skilled in the art may be made in the arrangement, operation, and details of the methods and systems of the present invention disclosed herein without departing from the scope of the claimed invention.

The above specification, examples and data provide a description of the manufacture and use of the invention. Since many embodiments of the invention can be made without departing from the spirit and scope of the invention, the invention resides in the claims hereinafter appended.

We claim:

1. An implantable device for chronic placement in a patient's body, the device for use in combination with a flow of a fluid having a biologic component and subject to an adverse response to shear stress, the device including a surface in contact with the flow of the fluid, the surface comprising:
   a longitudinal direction extending from a leading end toward a trailing end and aligned with a direction of the flow, the surface susceptible to inducing boundary layer formation within the flow sufficient for a resulting shear stress to induce the adverse response, and
   a surface feature projecting into the flow sufficient to induce boundary layer tripping in the flow to retard growth of boundary layer formation along the length and create advected vortices, wherein the surface feature is a movable protuberance.

2. A device according to claim 1 wherein the fluid is blood and the adverse response is a thrombosis formation response.

3. A device according to claim 1 wherein the biological component is a cell or cell component and said adverse response is cell injury from the resulting shear stress.

4. A device according to claim 1 wherein the surface is in contact with blood flow.

5. A device according to claim 1 wherein the plurality of projections are located along the length of the surface with the projections dimensioned and positioned to induce the advected vortices in the flow on a trailing side of the projections.

6. A device according to claim 1 wherein the surface further includes a plurality of indentations along the length of the surface with the indentations dimensioned and positioned to induce the advected vortices in the flow on a trailing side of the plurality of indentations.

7. A device according to claim 5 wherein the surface surrounds the flow of fluid and defines a cross-sectional area transverse to the direction of flow and a first reduction in the area attributable to the projections does not adversely affect flow rate through the device.

8. A device according to claim 1 wherein a spacing between the projections is sized to avoid stagnant flow formation in the spacing.

9. A device according to claim 1 wherein the surface feature is adapted to induce boundary layer tripping in a first flow direction and not in a second flow direction.

10. A device according to claim 1, wherein the surface feature projecting into the flow are sufficient to induce formation of secondary counter-rotating streamwise vortex pairs.

11. A device according to claim 1, wherein the surface feature is flexible.

12. A device according to claim 1, wherein the surface feature is located at the trailing end of the surface.

13. A device according to claim 1, wherein, the surface feature is arranged to break up spanwise vortices and reduce surface shear stress and momentum loss.

14. A device according to claim 1, wherein the surface feature is arranged to prevent eddies from transporting high speed fluid close to the flat surface.

15. A device according to claim 1, wherein the surface feature is configured to oscillate.

16. A device according to claim 1, wherein the surface feature is non-continuous.

17. A device according to claim 1, wherein the surface is otherwise smooth except for the surface feature protruding from the surface.

18. A device according to claim 1, wherein the surface feature inhibits flow stagnation.

* * * * *